US011104352B2

(12) United States Patent
Jones et al.

(10) Patent No.: US 11,104,352 B2
(45) Date of Patent: Aug. 31, 2021

(54) VEHICLE CONTROL SYSTEM

(71) Applicant: UATC, LLC, San Francisco, CA (US)

(72) Inventors: Morgan D. Jones, Pittsburgh, PA (US); Michael John Dacko, Oakmont, PA (US); Brian Thomas Kirby, Pittsburgh, PA (US)

(73) Assignee: UATC, LLC, San Francisco, CA (US)

( * ) Notice: Subject to any disclaimer, the term of this patent is extended or adjusted under 35 U.S.C. 154(b) by 312 days.

(21) Appl. No.: 16/267,468

(22) Filed: Feb. 5, 2019

(65) Prior Publication Data

US 2019/0176843 A1 Jun. 13, 2019

Related U.S. Application Data

(63) Continuation of application No. 15/440,510, filed on Feb. 23, 2017, now Pat. No. 10,220,857.

(51) Int. Cl.
*B60W 50/08* (2020.01)
*G05D 1/00* (2006.01)
(Continued)

(52) U.S. Cl.
CPC .......... *B60W 50/082* (2013.01); *B60W 10/18* (2013.01); *B60W 10/20* (2013.01);
(Continued)

(58) Field of Classification Search
CPC .... B60W 50/082; B60W 10/18; B60W 10/20; B60W 50/029; B60W 40/08;
(Continued)

(56) References Cited

U.S. PATENT DOCUMENTS 8,768,539 B1 7/2014 Clement et al.
2007/0198145 A1 8/2007 Norris et al.
(Continued)

FOREIGN PATENT DOCUMENTS

AU 2012200702 9/2012
CN 102495612 6/2012
(Continued)

OTHER PUBLICATIONS

Horwiek et al., "Strategy and Architecture of a Safety Concept for Fully Automatic and Autonomous Driving Assistance Systems", Institute of Electrical and Electronics Engineers Intelligent Vehicles Symposium, San Diego, California, Jun. 21-24, 2010, pp. 955-960.
(Continued)

*Primary Examiner* — Behrang Badii
(74) *Attorney, Agent, or Firm* — Dority & Manning, P.A.

(57) ABSTRACT

Systems and methods for controlling a failover response of an autonomous vehicle are provided. In one example embodiment, a method includes determining, by one or more computing devices on-board an autonomous vehicle, an operational mode of the autonomous vehicle. The autonomous vehicle is configured to operate in at least a first operational mode in which a human driver is present in the autonomous vehicle and a second operational mode in which the human driver is not present in the autonomous vehicle. The method includes detecting a triggering event associated with the autonomous vehicle. The method includes determining actions to be performed by the autonomous vehicle in response to the triggering event based at least in part on the operational mode. The method includes providing one or more control signals to one or more of the systems on-board the autonomous vehicle to perform the one or more actions in response to the triggering event.

20 Claims, 6 Drawing Sheets

(51) Int. Cl.
*B60W 10/18* (2012.01)
*B60W 10/20* (2006.01)
*B60W 50/029* (2012.01)
*G01S 19/42* (2010.01)
*G01C 21/34* (2006.01)
*B60W 40/08* (2012.01)
*B60K 28/06* (2006.01)
*A61B 5/00* (2006.01)
*A61B 3/11* (2006.01)

(52) U.S. Cl.
CPC ......... *B60W 50/029* (2013.01); *G05D 1/0055* (2013.01); *G05D 1/0061* (2013.01); *G05D 1/0088* (2013.01); *A61B 3/11* (2013.01); *A61B 5/00* (2013.01); *B60K 28/06* (2013.01); *B60W 40/08* (2013.01); *B60W 50/085* (2013.01); *B60W 2040/0881* (2013.01); *B60W 2420/42* (2013.01); *B60W 2420/52* (2013.01); *G01C 21/34* (2013.01); *G01S 19/42* (2013.01); *G05D 2201/0213* (2013.01)

(58) Field of Classification Search
CPC ....... B60W 50/085; B60W 2040/0881; B60W 2420/42; B60W 2420/52; G05D 1/0055; G05D 1/0061; G05D 1/0088; G05D 2201/0213; A61B 3/11; B60K 28/06; G01C 21/34; G01S 19/42
See application file for complete search history.

(56) References Cited

U.S. PATENT DOCUMENTS

| | | |
|---|---|---|
| 2014/0244096 A1 | 8/2014 | An et al. |
| 2014/0303827 A1 | 10/2014 | Dolgov et al. |
| 2015/0134178 A1 | 5/2015 | Minoiu-Enache |
| 2015/0142244 A1 | 5/2015 | You et al. |
| 2015/0309510 A1* | 10/2015 | Cudak .................. B60W 30/16 701/28 |
| 2015/0339928 A1 | 11/2015 | Ramanujam |
| 2015/0348335 A1 | 12/2015 | Ramanujam |
| 2016/0214596 A1 | 7/2016 | Gluga et al. |
| 2016/0244135 A1* | 8/2016 | Farber .................. B63G 8/001 |
| 2017/0021765 A1 | 1/2017 | Mori et al. |
| 2017/0021837 A1 | 1/2017 | Ebina |
| 2017/0088143 A1* | 3/2017 | Goldman-Shenhar ....................... B60W 50/08 |
| 2017/0166222 A1* | 6/2017 | James .................. B60W 40/09 |
| 2017/0248952 A1* | 8/2017 | Perkins ................ G05D 1/0061 |
| 2017/0248957 A1* | 8/2017 | Delp ...................... B60W 30/00 |
| 2017/0285637 A1 | 10/2017 | Jones et al. |
| 2017/0285639 A1 | 10/2017 | Jones et al. |
| 2017/0364070 A1 | 12/2017 | Oba |
| 2018/0074514 A1 | 3/2018 | Switkes et al. |
| 2018/0120855 A1* | 5/2018 | Christiansen ........ G05D 1/0212 |
| 2018/0164808 A1* | 6/2018 | Prokhorov .......... B60W 10/18 |
| 2018/0164823 A1* | 6/2018 | She ........................ G08G 1/165 |
| 2019/0162549 A1* | 5/2019 | Fouad ................ G01C 21/3484 |
| 2019/0263419 A1* | 8/2019 | Prakah-Asante ..... B60W 40/09 |
| 2021/0116256 A1* | 4/2021 | Konrardy ............... G08G 1/166 |

FOREIGN PATENT DOCUMENTS

| | | |
|---|---|---|
| CN | 104064050 | 9/2014 |
| CN | 104477113 | 4/2015 |
| CN | 105818810 | 8/2016 |
| JP | H11184521 | 7/1999 |
| JP | 2008071253 | 3/2008 |
| JP | 2015133050 | 10/2015 |
| JP | 2015228152 | 12/2015 |
| JP | 5877574 | 3/2016 |
| JP | 2016210417 | 12/2016 |
| WO | WO 2018038131 | 3/2018 |

OTHER PUBLICATIONS

Reschka et al., "A Surveillance and Safety System based on Performance Criteria and Functional Degradation for an Autonomous Vehicle", Institute of Electrical and Electronics Engineers Intelligent Transportation systems, Anchorage, Alaska, Sep. 16-19, 2012, 6 pages.

Wei et al., "Towards a Viable Autonomous Driving Research Platform". Institute of Electrical and Electronics Engineers Intelligent Vehicles Symposium, Gold Coast, Austrilia, Jun. 23-26, 2013, 8 pages.

International Preliminary Report on Patentability for Application No. PCT/US2018/018600, dated Sep. 6, 2019, 10 pages.

* cited by examiner

VEHICLE CONTROL SYSTEM

PRIORITY CLAIM

The present application is a continuation of U.S. application Ser. No. 15/440,510 having a filing date of Feb. 23, 2017. Applicant claims priority to and benefit of all such applications and incorporate all such applications herein by reference.

FIELD

The present disclosure relates generally to controlling the response of an autonomous vehicle to a detected triggering event based on the vehicle's operational mode.

BACKGROUND

An autonomous vehicle can perceive its surroundings by using various sensor apparatuses and determining its position on the basis of the information associated with its surroundings. This can allow an autonomous vehicle to navigate without human intervention and, in some cases, even omit the use of a human driver altogether. In some cases, an autonomous vehicle may be monitored by a remote tracking system. However, such monitoring can be subject to potential communication latencies.

SUMMARY

Aspects and advantages of embodiments of the present disclosure will be set forth in part in the following description, or may be learned from the description, or may be learned through practice of the embodiments.

One example aspect of the present disclosure is directed to a computer-implemented method of controlling a failover response of an autonomous vehicle. The method includes determining, by one or more computing devices on-board an autonomous vehicle, an operational mode of the autonomous vehicle. The autonomous vehicle is configured to operate in at least a first operational mode in which a human driver is present in the autonomous vehicle and a second operational mode in which the human driver is not present in the autonomous vehicle. The method includes detecting, by the one or more computing devices, a triggering event associated with the autonomous vehicle. The method includes determining, by the one or more computing devices, one or more actions to be performed by one or more systems on-board the autonomous vehicle in response to the triggering event. The one or more actions are based at least in part on whether the autonomous vehicle is in the first operational mode or the second operational mode. The method includes providing, by the one or more computing devices, one or more control signals to one or more of the systems on-board the autonomous vehicle to perform the one or more actions in response to the triggering event.

Another example aspect of the present disclosure is directed to a control system for controlling a failover response of an autonomous vehicle. The system includes one or more processors on-board an autonomous vehicle and one or more memory devices on-board the autonomous vehicle. The one or more memory devices store instructions that when executed by the one or more processors cause the one or more processors to perform operations. The operations include detecting a triggering event associated with an autonomous vehicle configured to operate in a plurality of operational modes. The plurality of operational modes include a first operational mode in which a human driver is present in the autonomous vehicle and a second operational mode in which the human driver is not present in the autonomous vehicle. The operations include determining one or more actions to be performed by one or more systems on-board the autonomous vehicle in response to the detection of the triggering event. The one or more actions are based at least in part on whether the autonomous vehicle is in the first operational mode or the second operational mode. The operations include providing one or more control signals to the one or more systems on-board the autonomous vehicle to perform the one or more actions.

Yet another example aspect of the present disclosure is directed to an autonomous vehicle including one or more systems on-board the autonomous vehicle, one or more processors on-board the autonomous vehicle, and one or more memory devices on-board the autonomous vehicle. The one or more memory devices store instructions that when executed by the one or more processors cause the one or more processors to perform operations. The operations include determining an operational mode of the autonomous vehicle. The autonomous vehicle is configured to operate in at least a first operational mode in which a human driver is present in the autonomous vehicle and a second operational mode in which the human driver is not present in the autonomous vehicle. The operations include detecting a triggering event associated with the autonomous vehicle. The operations include determining one or more actions to be performed by one or more of the systems on-board the autonomous vehicle in response to the triggering event. The one or more actions are based at least in part on whether the human driver is present in the autonomous vehicle. The operations include providing one or more control signals to one or more of the systems on-board the autonomous vehicle to perform the one or more actions.

Other example aspects of the present disclosure are directed to systems, methods, vehicles, apparatuses, tangible, non-transitory computer-readable media, user interfaces, and memory devices for controlling a failover response of an autonomous vehicle.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
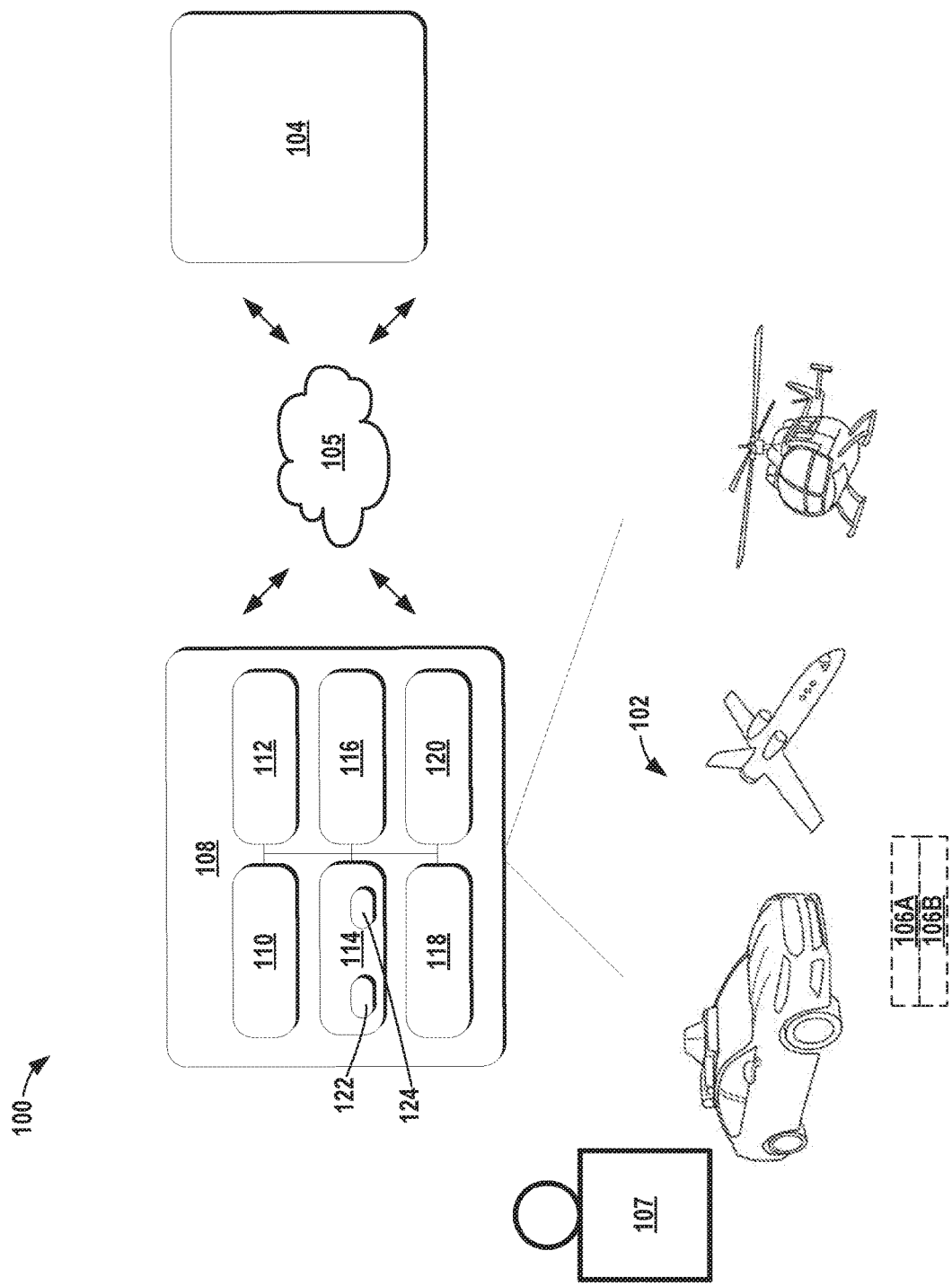
FIG. 1 depicts an example system overview according to example embodiments of the present disclosure.

Reference now will be made in detail to embodiments, one or more example(s) of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to determining the operational mode of an autonomous vehicle and controlling the failover response of an autonomous vehicle to a detected triggering event. A failover response can be the response, such as an action, taken by the autonomous vehicle (e.g., its computing system) based at least in part on a triggering event associated with the vehicle. A triggering event can be an occurrence associated with the autonomous vehicle that causes the autonomous vehicle to change from a normal operating state (e.g., in which the autonomous vehicle autonomously navigates) to a failover operating state (e.g., that allows manual vehicle control, stops the motion of the autonomous vehicle). The autonomous vehicle can respond more appropriately to the detected triggering event because the response is based on the operational mode of the vehicle. For instance, an autonomous vehicle can be configured to drive, navigate, operate, etc. in a plurality of operational modes. In a first operational mode, a human driver can be present in the autonomous vehicle. The autonomous vehicle can also operate in a second operational mode in which no human driver is present in the vehicle. As such, the vehicle must autonomously navigate without interaction from the human driver. The autonomous vehicle can include a "drive-by-wire" control system that is configured to detect the current operational mode of the autonomous vehicle. Moreover, the control system can detect a triggering event associated with the autonomous vehicle and respond in accordance with the vehicle's current operational mode. For example, the control system may detect a communication error that prevents the vehicle control components (e.g., steering component, braking component) from receiving signals from the vehicle's autonomy system (e.g., configured to plan vehicle motion). Such error can hinder the vehicle's ability to autonomously navigate. Accordingly, the control system can determine one or more actions to address the triggering event based at least in part on the operational mode of the autonomous vehicle. For example, in the event that a human driver is present in the autonomous vehicle (e.g., operating in the first operational mode), the control system can cause the autonomous vehicle to enter into a manual control mode that allows the human driver to manually control the vehicle. In the event that no human driver is present in the autonomous vehicle (e.g., operating in the second operational mode), the control system can cause the vehicle to decelerate to a stopped position. In this way, the control system can be configured to customize the failover response of the autonomous vehicle based at least in part on the vehicle's operational mode, increasing vehicle and passenger safety.

More particularly, an autonomous vehicle (e.g., a ground-based vehicle) can be configured to operate in a plurality of operational modes. For example, an autonomous vehicle can operate in a first operational mode in which a human driver (e.g., safety driver) is present in the autonomous vehicle. While in the first operational mode, the autonomous vehicle can be configured to operate in a fully autonomous (e.g., self-driving) manner in which the autonomous vehicle can drive and navigate with minimal and/or no interaction from the human driver present in the vehicle. Additionally, or alternatively, the autonomous vehicle can operate in a semi-autonomous manner in which the vehicle can operate with some interaction from the human driver present in the vehicle. In some implementations, the autonomous vehicle can enter into a manual control mode in which the vehicle is controllable by the human driver and is prohibited from performing an autonomous navigation (e.g., autonomous driving). The autonomous vehicle can also operate in a second operational mode in which the human driver is not present in the autonomous vehicle. In such a case, the autonomous vehicle can operate in a fully autonomous manner with no human driver interaction. In some implementations, the operational mode can be set by human interaction (e.g., via a physical interface), as further described herein. In some implementations, individuals inside the vehicle (e.g., a driver, passengers) may not have the ability to set and/or change the vehicle from one operational mode to another. Rather, the operation mode of the vehicle can be set off-board (e.g., from a remote computing device associated with a vehicle owner, vehicle fleet operator, other entity).

The autonomous vehicle can include a vehicle computing system that implements a variety of systems on-board the autonomous vehicle. For instance, the vehicle computing system can include one or more data acquisition system(s) (e.g., sensors, image capture devices), one or more human machine interface system(s) (e.g., physical interface buttons, user interfaces displayed via a display device), an autonomy system (e.g., for planning autonomous navigation), one or more vehicle control components (e.g., for controlling braking, steering, powertrain), etc. The vehicle computing system can also include a "drive-by-wire" control system that can be separate from one or more other on-board systems (e.g., separate from the autonomy system, separate from the vehicle control components). The control system can include one or more computing device(s) configured to perform a variety of functions to control the failover response of the autonomous vehicle in the event of a vehicle triggering event.

The control system can determine an operational mode of the autonomous vehicle. For example, the control system can receive (e.g., from another vehicle system) data indicative of the operational mode of the autonomous vehicle. In some implementations, the autonomous vehicle can include a physical interface (e.g., adjustable key switch) that is configured to mechanically toggle the vehicle between the first operational mode (e.g., human driver present) and the second operational mode (e.g., no human driver present). The control systems can determine the operational mode of the autonomous vehicle based at least in part on the position of the physical interface. In some implementations, the presence of a human driver can be detected based at least in part on a change in a condition associated with the interior of the autonomous vehicle. For instance, the autonomous vehicle can include one or more sensor(s) configured to detect a weight load force of the human driver (e.g., in a driver's seat) and/or whether a seat belt of the human driver has been securely fastened.

The control system can detect a triggering event associated with the autonomous vehicle. For example, the control system can monitor and/or receive data indicative of one or more motion control instruction(s) from the vehicle's autonomy system. The control system can detect whether there has been a communication error, such that the autonomy system is unable to communicate such signals to the vehicle control components (and/or the control system itself). Additionally, or alternatively, the triggering event can be associated with a signal provided by an interface (e.g., mushroom button) on-board the vehicle (e.g., for user initiated requests) and/or provided by a remote computing device that is remote from the vehicle (e.g., from a central operations control center). The signal can indicate a specific vehicle triggering event (e.g., hardware overheating, memory storage low), that the vehicle is to stop moving, that the vehicle is to change operating state, etc. In some implementations, the triggering event can include a signal (e.g., a stop motion signal) that is associated with a sensor of the vehicle's bumper.

The control system can determine one or more action(s) to be performed by the systems on-board the autonomous vehicle in response to the triggering event. The action(s) can be based at least in part on whether the autonomous vehicle is in the first operational mode (e.g., human driver present) or the second operational mode (e.g., no human driver present). For example, in the event that the human driver is not present in the autonomous vehicle, the action(s) can include stopping a motion of the vehicle. Such a response can be appropriate when the vehicle is unable to autonomously navigate (e.g., due to a lack of communicability with the autonomy system). As such, the control system can send control signal(s) to the vehicle control components (e.g., braking, steering) to decelerate and/or change the direction of the vehicle until the vehicle reaches a stopped position. In the event that a human driver is present in the autonomous vehicle, the action(s) can include allowing the human driver to manually control the autonomous vehicle. In such a case, the control system can send control signal(s) to cause the autonomous vehicle to enter into a manual control mode, whereby the vehicle is controlled based at least in part on user input from the human driver (e.g., via the steering wheel, foot/hand brake interface, accelerator interface).

In some implementations, the control system can reset the autonomous vehicle such that it can continue to autonomously navigate. For example, after performance of the action(s) (e.g., to facilitate stopping, to provide manual control), the control system can receive data indicating that the autonomous vehicle is in a ready state, in which the vehicle is ready to return to autonomous navigation (e.g., without interaction from the human driver). In some implementations, the control system can receive the data indicating that the vehicle is ready to return to autonomous navigation from a computing device located onboard the vehicle. For example, such an on-board computing device can be one that identified the occurrence of the triggering event (e.g., critical memory storage error). The on-board computing device can then later identify that the triggering event has been cleared, addressed, etc. In some implementations, such data can be provided by a remote computing device (e.g., of an operations computing system) and/or via user input from the human driver (e.g., relinquishing control of the vehicle after the triggering event has been addressed). The control system can send control signal(s) to one or more of the system(s) on-board the autonomous vehicle (e.g., autonomy system, vehicle control components) to resume autonomous navigation (and motion) of the vehicle.

The system and methods described herein may provide a number of technical effects and benefits. For instance, the vehicle's control system can locally (e.g., on-board the vehicle) detect a triggering event and tailor the failover response to the operational mode of the vehicle. This can help the vehicle computing system to avoid potential mode confusion as well as to avoid implementing an inappropriate failover response. Moreover, the autonomous vehicle can appropriately respond to a triggering event (e.g., given the vehicle's mode) without relying on a computing system that is remote from the vehicle (e.g., a central operations system). This can allow the autonomous vehicle to avoid potential latency issues that can arise when communicating with remote computing devices (e.g., due to poor network connectivity, data upload/download). The autonomous vehicle can also avoid potential latency issues that can arise from remote computing device(s) processing multiple vehicle triggering event diagnostic requests (e.g., in the order they are received). By reducing the vehicle computing system's reliance on remote computing devices, the systems and methods of the present disclosure can reduce stress on the vehicle's communication interfaces, bandwidth usage, network traffic, etc.

Furthermore, by determining a failover response on-board the autonomous vehicle, the systems and methods of the present disclosure can limit the allocation of processing and storage resources of a central operations computing system that are required for such analysis. The saved resources can be allocated to other functions of the operations computing systems, such as the processing of service requests, vehicle routing, etc. In this way, the systems and methods according to example aspects of the present disclosure have a technical effect of providing a computationally efficient approach to controlling a failover response of an autonomous vehicle while saving computational resources for other functions.

The systems and methods of the present disclosure also provide an improvement to vehicle computing technology, such as autonomous vehicle computing technology. For instance, the systems and methods herein enable the vehicle technology to locally detect and appropriately respond to triggering events associated with the autonomous vehicle. For example, the systems and methods can allow one or more computing device(s) (e.g., of a control system) on-board an autonomous vehicle to determine an operational mode of the autonomous vehicle. As described herein, the autonomous vehicle can be configured to operate in at least a first operational mode in which a human driver is present in the autonomous vehicle and a second operational mode in which the human driver is not present in the autonomous vehicle. The computing device(s) can detect a triggering event associated with the autonomous vehicle. The computing device(s) can determine one or more action(s) to be performed by one or more system(s) on-board the autonomous vehicle in response to the triggering event. Particularly, the one or more action(s) can be based at least in part on whether the autonomous vehicle is in the first operational mode or the second operational mode. The computing devices can provide one or more control signal(s) to one or more of the system(s) on-board the autonomous vehicle to perform the action(s). In this way, the computing device(s) can tailor the failover response of the vehicle based at least in part on the operational mode of the vehicle (e.g., whether a human driver is present). This can allow the computing device(s) to more accurately determine the correct response to a triggering event, increasing vehicle and passenger safety.

Moreover, the computing device(s) can be included in a control system that is separate and apart from the other systems on-board the autonomous vehicle (e.g., autonomy system, vehicle control component). As such, the control system can include a simplified hardware architecture that is easier to upgrade, implement mode/redundancy checks, etc. This can also allow the computing device(s) to focus its computational resources on the task of triggering event detection and response determination, rather than allocating its resources to perform other vehicle functions (e.g., autonomous motion planning, motion plan implementation). Such use of resources can allow the computing device(s) to provide a more efficient, reliable, and accurate response to the detection of a vehicle triggering event. Additionally, the other systems on-board the autonomous vehicle can focus on their core functions, rather than allocating resources to the functions of the control system. Thus, the systems and methods of the present disclosure can save the computational resources of these other vehicle systems, while further increasing performance of the control system.

With reference now to the FIGS., example embodiments of the present disclosure will be discussed in further detail. FIG. 1 depicts an example system 100 according to example embodiments of the present disclosure. The system 100 can include a vehicle 102 and one or more remote computing device(s) 104. The remote computing device(s) 104 can be associated with a vehicle owner, a fleet operator, maintenance and/or monitoring entity, a central operations computing system, and/or another entity that is associated with the vehicle 102. Additionally, or alternatively, the entity can be a service provider that provides one or more vehicle service(s) to a plurality of users via a fleet of vehicles that includes, for example, the vehicle 102. The vehicle service(s) can include transportation services (e.g., rideshare services), courier services, delivery services, and/or other types of services. The vehicle service(s) can transport and/or deliver passengers as well as items such as but not limited to food, animals, freight, purchased goods, etc.

The remote computing device(s) 104 can include multiple components for performing various operations and functions. For example, the remote computing device(s) 104 can include and/or otherwise be associated with one or more computing device(s) that are remote from the vehicle 102. The one or more computing device(s) can include one or more processor(s) and one or more memory device(s). The one or more memory device(s) can store instructions that when executed by the one or more processor(s) cause the one or more processor(s) to perform operations and functions (e.g., for monitoring, communicating with the vehicle 102).

The remote computing device(s) 104 can communicate with the vehicle 102 via one or more communications network(s) 105. The communications network(s) 105 can include various wired and/or wireless communication mechanisms (e.g., cellular, wireless, satellite, microwave, and radio frequency) and/or any desired network topology (or topologies). For example, the communications network(s) 105 can include a local area network (e.g. intranet), wide area network (e.g. Internet), wireless LAN network (e.g., via Wi-Fi), cellular network, a SATCOM network, VHF network, a HF network, a WiMAX based network, and/or any other suitable communications network (or combination thereof) for transmitting data to and/or from the vehicle 102.

The vehicle 102 can be a ground-based vehicle (e.g., an automobile, truck, bus), an aircraft, and/or another type of vehicle. The vehicle 102 can be an autonomous vehicle that can drive, navigate, operate, etc. with minimal and/or no interaction from a human driver. The vehicle 102 can be configured to operate in a plurality of operational modes 106A-B. For example, the plurality of operational modes can include a first operational mode 106A in which a human driver 107 (e.g., safety driver) is present in the vehicle 102. While in the first operational mode 106A, the vehicle 102 can be configured to operate in a semi-autonomous manner in which the vehicle 102 can operate with some interaction from the human driver 107 present in the vehicle 102 (e.g., toggling between fully autonomous navigation and allowing for at least some manual control of the vehicle 102). Additionally, or alternatively, while in the first operational mode 106A, the vehicle 102 can operate in fully autonomous (e.g., self-driving) manner in which the vehicle 102 can drive and navigate with minimal and/or no interaction from the human driver 107 present in the vehicle 102. In some implementations, the vehicle 102 can enter into a manual control mode in which the vehicle 102 is controllable by the human driver and is prohibited from performing an autonomous navigation (e.g., prohibited from autonomous driving).

The plurality of operational modes can also include a second operational mode 106B in which the human driver 107 is not present in the vehicle 102. While in the second operational mode 106B, the vehicle 102 can operate in a fully autonomous manner with no human driver present in the vehicle.

The operational modes 106A-B of the vehicle 102 can be set with and/or without interaction from a human present in the vehicle 102. For example, in some implementations, the operational mode 106A-B can be set by human interaction (e.g., via a physical interface), as further described herein. In some implementations, individuals inside the vehicle (e.g., a driver, passengers) may not have the ability to change the vehicle 102 from one operational mode to another. Rather, the operational mode of the vehicle 102 can be set off-board (e.g., from a remote computing device 104 associated with a vehicle owner, vehicle fleet operator, other entity).

The vehicle 102 can include a vehicle computing system 108 that implements a variety of systems on-board the vehicle 102. The vehicle computing system 108 can include one or more computing device(s) for implementing the systems. For instance, the vehicle computing system can include a communications system 110, one or more human machine interface system(s) 112, one or more data acquisition system(s) 114, an autonomy system 116, one or more vehicle control component(s) 118, and a "drive-by-wire" control system 120. One or more of these system(s) can be configured to communicate with one another via a communication channel. The communication channel can include one or more data bus(es) (e.g., controller area network (CAN), on-board diagnostics connector (e.g., OBD-II), and/or a combination of wired and/or wireless communication links). The on-board systems can send and/or receive data, messages, signals, etc. amongst one another via the communication channel.

The communications system 110 can be configured to allow the vehicle computing system 108 (and its subsystems) to communicate with other computing devices. For example, the vehicle computing system 108 can use the communications system 110 to communicate with the remote computing device(s) 104 over the network(s) 105 (e.g., via one or more wireless signal connections). The communications system 110 can include any suitable components for interfacing with one or more network(s), including for example, transmitters, receivers, ports, controllers, antennas, or other suitable components that can help facilitate communication with one or more remote computing device(s) that are remote from the vehicle 102.

The human machine interface system(s) 112 can be configured to allow interaction between a user (e.g., human) and the vehicle 102 (e.g., the vehicle computing system 108). The human machine interface system(s) 112 can include a variety of interfaces for the user to input and/or receive information from the vehicle computing system 108. The human machine interface system(s) 112 can include one or more input device(s) (e.g., touchscreens, keypad, touchpad, knobs, buttons, sliders, switches, mouse, gyroscope, microphone, other hardware interfaces) configured to receive user input. The human machine interface system(s) 112 can include a user interface (e.g., graphical user interface, conversational and/or voice interfaces, chatter robot, gesture interface, other interface types) for receiving user input. The human machine interface(s) 112 can also include one or more output device(s) (e.g., display devices, speakers, lights) to output data associated with the interfaces.

In some implementations, human machine interface system(s) 112 can include an interface configured to adjust the operational mode 106A-B of the vehicle 102. For example, the vehicle 102 can include an interface, such as a physical interface (e.g., adjustable key switch), that is adjustable between a first position and a second position. Adjustment of this interface can change the operational mode of the vehicle 102. For example, the vehicle 102 can be configured to operate in the first operational mode 106A (e.g., human driver present) when the interface is in the first position. The vehicle 102 can be configured to operate in the second operational mode 106B (e.g., no human driver present) when the interface is in the second position. In some implementations, the vehicle 102 can include an indicator that is configured to display or otherwise communicate the current operational mode of the vehicle 102, such as via an output device provided as part of human machine interface(s) 112.

The vehicle 102 can also be configured to enter into a ready state. The ready state can indicate that the vehicle 102 is ready to operate (and/or return to) an autonomous navigation mode. For example, in the event that a human driver 107 is present in the vehicle 102, the human driver 107 may indicate (e.g., via interaction with an interface) that the vehicle 102 is ready to operate in an autonomous navigation mode. Additionally, or alternatively, a computing device on-board the vehicle 102 can be configured to determine whether the vehicle 102 is in the ready state. In some implementations, a remote computing device 104 (e.g., associated with an operations control center) can indicate that the vehicle 102 is ready to begin and/or resume autonomous navigation.

The data acquisition system(s) 114 can include various devices configured to acquire data associated with the vehicle 102. This can include data associated with one or more of the vehicle's system(s) (e.g., health data), the vehicle's interior, the vehicle's exterior, the vehicle's surroundings, the vehicle users (e.g., driver, passenger), etc. The data acquisition system(s) 114 can include, for example, one or more image capture device(s) 122. The image capture device(s) 122 can include one or more camera(s), light detection and ranging (or radar) device(s) (LIDAR systems), two-dimensional image capture devices, three-dimensional image capture devices, static image capture devices, dynamic (e.g., rotating) image capture devices, video capture devices (e.g., video recorders), lane detectors, scanners, optical readers, electric eyes, and/or other suitable types of image capture devices. The image capture device(s) 122 can be located in the interior and/or on the exterior of the vehicle 102. The one or more image capture device(s) 122 can be configured to acquire image data to be used for operation of the vehicle 102, for example, in an autonomous mode.

Additionally, or alternatively, the data acquisition systems 114 can include one or more sensor(s) 124. The sensor(s) 124 can include impact sensors, motion sensors, pressure sensors, temperature sensors, humidity sensors, RADAR, sonar, radios, medium-range and long-range sensors (e.g., for obtaining information associated with the vehicle's surroundings), global positioning system (GPS) equipment, proximity sensors, and/or any other types of sensors for obtaining data associated with the vehicle 102. The data acquisition systems 114 can include one or more sensor(s) 124 dedicated to obtaining data associated with a particular aspect of the vehicle 102, such as, the vehicle's fuel tank, engine, oil compartment, wipers, etc. The sensor(s) 124 can also, or alternatively, include sensor(s) associated with one or more mechanical and/or electrical components of the vehicle 102. For example, one or more of the sensor(s) 124 can be configured to detect whether a vehicle door, is in an open or closed position, the vehicle's available data storage, the vehicle's charge level, etc.

One or more of the sensor(s) 124 can be configured to detect a change in a condition associated with the interior of the vehicle 102. For example, a sensor can be configured to detect a weight load in a driver's seat of the vehicle 102. Additionally or alternatively, a sensor can be configured to detect the position of a seat belt associated with the driver seat (e.g., whether the buckle is in a fastened position or an unfastened position). In this way, the sensor can be configured to collect data indicative of the whether a human driver 107 is present in the vehicle 102.

In addition to the data acquired via the data acquisition system(s) 114, the vehicle computing system 108 can also be configured to obtain map data. For instance, a computing device of the vehicle 102 (e.g., within the autonomy system 116) can be configured to receive map data from one or more remote computing device(s). The map data can provide information regarding: the identity and location of different roadways, road segments, buildings, or other items; the location and directions of traffic lanes (e.g., the boundaries, location, direction, etc. of a parking lane, a turning lane, a bicycle lane, or other lanes within a particular travel way); traffic control data (e.g., the location and instructions of signage, traffic lights, or other traffic control devices); and/or any other map data that provides information that assists the computing system in comprehending and perceiving its surrounding environment and its relationship thereto.

The autonomy system 116 can be configured to control the operation of the vehicle 102 (e.g., to operate autonomously). For instance, the autonomy system 116 can obtain the data associated with the vehicle 102 (e.g., acquired by the data acquisition system(s) 114) and/or the map data. The autonomy system 116 can control various functions of the vehicle 102 based, at least in part, on the acquired data associated with the vehicle 102 and/or the map data. For example, the autonomy system 116 can include various models to perceive road features, signage, and/or objects (e.g., other vehicles, bikes, people, animals, etc.) based on the data acquired by the data acquisition system(s) 114, map data, and/or other data. The autonomy system 116 can be configured to predict the position and/or movement (or lack thereof) of such elements. The autonomy system 116 can be configured to plan the motion of the vehicle 102 based, at least in part, on such predictions.

The autonomy system 116 can implement the planned motion to appropriately navigate the vehicle 102 with minimal or no human intervention. For instance, the autonomy system 116 can determine a position and/or route for the vehicle 102 in real-time and/or near real-time. For instance, using acquired data, the autonomy system 116 can calculate one or more different potential vehicle routes (e.g., every fraction of a second). The autonomy system 116 can then select which route to take and cause the vehicle 102 to navigate accordingly. By way of example, the autonomy system 116 can calculate one or more different straight path(s) (e.g., including some in different parts of a current lane), one or more lane-change path(s), one or more turning path(s), and/or one or more stopping path(s). The vehicle 102 can select a path based, at last in part, based on an optimization algorithm that considers the costs of potential vehicle movements and seeks to determine optimized variables that make up the motion plan. Once selected, the autonomy system 116 can cause the vehicle 102 to travel according to the selected path by sending one or more control signals to the one or more vehicle control component(s) 118.

The vehicle control component(s) 118 can be configured to control the motion of the vehicle 102. For example, vehicle control component(s) 118 can include a steering component configured to control the heading and/or direction of the vehicle 102. Moreover, the vehicle control component(s) 118 can include a braking component configured to control the braking of the vehicle 102. The vehicle control component(s) 118 can include other components, such as an acceleration component configured to control the acceleration of the vehicle 102, a gear-shift component configured to control the gears of the vehicle 102, and/or other components (e.g., such as those associated with the vehicle's powertrain). The vehicle control components(s) 118 can be configured to receive signals indicating the planned motion of the vehicle 102 and control the vehicle 102 accordingly. Signals for controlling the vehicle control component(s) 118 in accordance with a motion plan can include, for example, signals turning one or more vehicle control component(s) 118 on and/or off, signals indicating a pedal position and/or pedal angle of an acceleration component and/or braking component, and/or signals indicating a position and/or angle of a steering component.

The control system 120 can be configured to control the failover response of the vehicle 102 in the event of a vehicle triggering event. In some implementations, the control system 120 can be separate from one or more of the other on-board system(s). For example, the control system can be separate from the autonomy system 116 and/or separate from the vehicle control component(s) 118. In other implementations, the control system 120 can be integrated as part of one or more other on-board systems and/or computing devices. The control system 120 can include one or more computing device(s) (e.g., one or more microcontroller(s)). The computing device(s) can include one or more processor(s) and one or more memory devices (e.g., all on-board the vehicle 102). The one or more memory device(s) can store instructions that when executed by the one or more processor(s) cause the one or more processor(s) to perform operations, such as those for controlling the failover response of the vehicle 102, as described herein.

Figure 2:
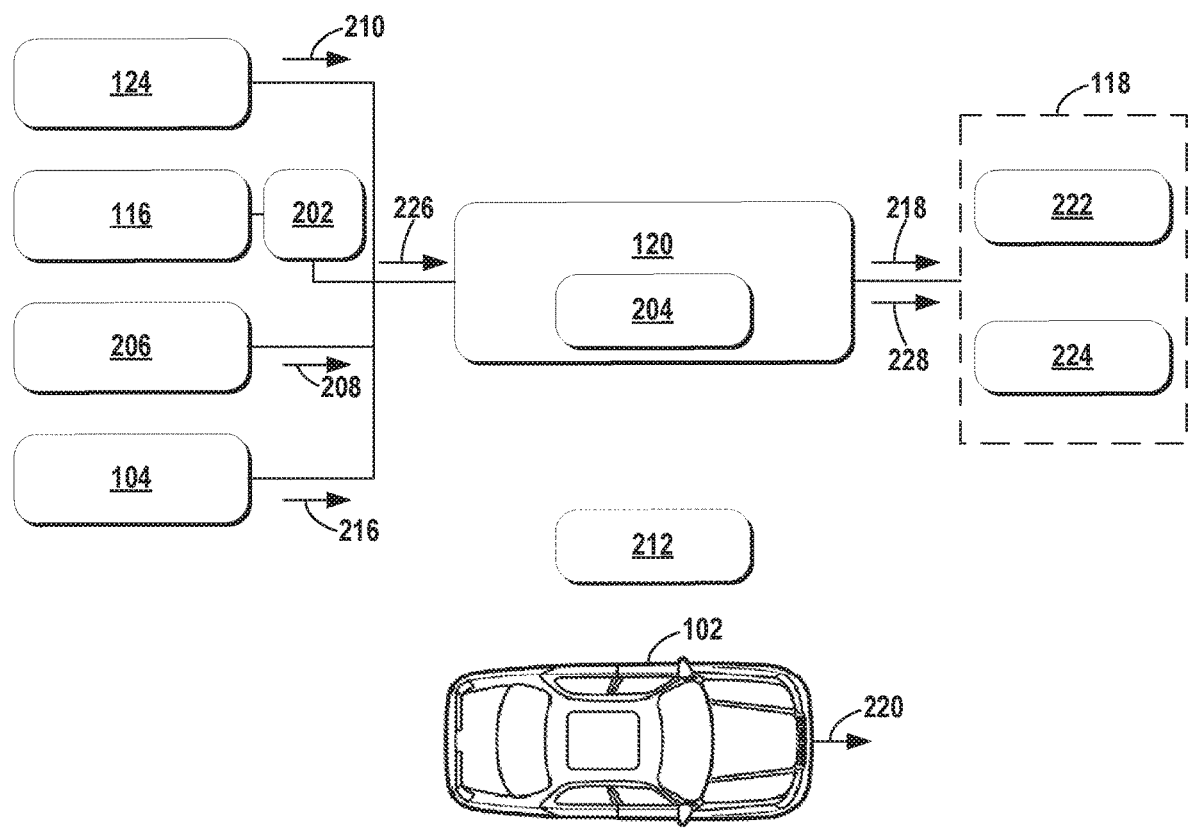
FIG. 2 depicts an example control system for controlling a failover response of a vehicle according to example embodiments of the present disclosure.

FIG. 2 depicts the control system 120 for controlling a failover response of a vehicle according to example embodiments of the present disclosure. As shown, the control system 120 can be configured as an intermediary between the autonomy system 116 and the vehicle control component(s) 118. For example, the control system 120 can be configured such that the control system 120 receives and/or monitors any data (and/or other communications) provided by the autonomy system 116 (e.g., including motion plan instructions) before the vehicle control component(s) 118 obtains such data and/or communications.

In some implementations, the autonomy system 116 can provide data indicative of a motion plan to a mobility controller 202. The mobility controller 202 can be configured to translate the motion plan into instructions. By way of example, the mobility controller 202 can translate a determined motion plan into instructions to adjust the steering of the vehicle 102 "X" degrees, apply 10% braking force, etc. The control system 120 can be configured to receive such instructions from the mobility controller 202 and generate control signals (e.g., indicative of the instructions) for the vehicle control components 118. In this way, communications that would affect the motion of the vehicle 102 can first go through and/or be monitored by the control system 120.

The control system 120 can include one or more computing device(s) 204 that are configured to control the failover response of the vehicle 102. For instance, the computing device(s) 204 can be configured to determine an operational mode 106A-B of the vehicle 102. The computing device(s) 204 can be configured to determine the operational mode 106A-B of the vehicle 102 based, at least in part, on data obtained via another vehicle component and/or computing device. By way of example, as described herein, the vehicle 102 (e.g., the human machine interface system(s) 112) can include a physical interface 206 (e.g., physical switch interface, touchscreen) that is adjustable between a first position and a second position to toggle the vehicle 102 between the first operational mode 106A (e.g., human driver (HD) present) and the second operational mode 106B (e.g., no human driver (NHD) present). The computing device(s) 204 can receive data 208 indicative of a position associated with the physical interface 206 on-board the vehicle 102. For example, the data 208 can indicate that the physical interface 206 is in the first position and, thus, the vehicle 102 is to operate in the first operational mode 106A. Alternatively, the data 208 can indicate that the physical interface 206 is in the second position and, thus, the vehicle 102 is to operate in the second operational mode 106B.

In some implementations, the computing device(s) 204 can determine whether the vehicle 102 is the first operational mode 106A or the second operational mode 106B based at least in part on data 210 provided by the sensor(s) 124. The data 210 can be indicative of the presence of the human driver 107 in the vehicle 102. The presence of the human driver 107 can be detectable based at least in part on a change in a condition associated with the vehicle 102 (e.g., the interior of the vehicle 102). For example, the condition associated with the vehicle 102 can include at least one of a weight load in a driver's seat of the autonomous vehicle and/or a position of a seat belt associated with the driver's seat. The sensor(s) 124 can be configured to detect a weight load in a driver's seat of the vehicle and/or a position of a seat belt associated with the driver's seat (e.g., which would be utilized by the human driver). In the event that a sufficient weight load is detected in the driver's seat and/or the seat belt of the driver's seat is in a fastened position, the sensor(s) 124 can send data 210 indicative of such conditions (and/or indicative of the human driver presence) to the computing device(s) 204. The computing device(s) 204 can determine that the vehicle 102 is to operate in the first operational mode 106A based at least in part on the data 210 (e.g., indicative of the change in condition, human driver presence). In the event that no weight load (or a nominal, insufficient weight load) is detected in the driver's seat and/or the seat belt of the driver's seat is in an unfastened position, the sensor(s) 124 can send data 210 indicative of such conditions (and/or indicative of no human driver presence) to the computing device(s) 204. In such a case, the computing device(s) 204 can determine that the vehicle 102 is to operate in the second operational mode 106B based at least in part on the data 210.

The computing device(s) 204 of the control system 120 can detect a triggering event 212 associated with the vehicle 102. In some implementations, the triggering event 212 can be a defect associated with a communicability between the computing device(s) 204 and another system of the vehicle 102. For example, the triggering event 212 can be associated with a lack of communicability with the autonomy system 116 of the vehicle 102. For instance, as described, the computing device(s) 204 can monitor and/or receive data indicative of motion control instruction(s) from the autonomy system 116 (and/or the mobility controller 202). The computing device(s) 204 can detect whether there has been a communication error, such that the autonomy system 116 (and/or the mobility controller 202) is unable to communicate with the vehicle control component(s) 118 (and/or the control system 120) to implement a motion plan. Such a triggering event can hinder the ability of the vehicle 102 to autonomously navigate. In some implementations, the triggering event 212 can include a signal (e.g., a stop motion signal) that is associated with an external motion detection system (e.g., detected objects at the rear, front bumper) of the vehicle 102.

In some implementations, the triggering event 212 can be associated with a user-initiated request (e.g., for manual control, to stop the vehicle 102). By way of example, as described herein, the vehicle 102 (e.g., the human machine interface system(s) 112) can include one or more interface(s) on-board the vehicle 102. At least one of the interface(s) (e.g., a mushroom button interface) can be configured to allow a human driver 107 to indicate that a triggering event has occurred with the vehicle 102 and/or that the vehicle 102 should be adjusted into the manual control mode to allow the human driver 107 manual control of the vehicle 102. Additionally, or alternatively, at least one of the interface(s) can allow a passenger to indicate the occurrence of a triggering event (and/or a passenger request to stop the vehicle 102). The computing device(s) 204 can receive data indicative of the user-initiated request (e.g., activation of the mushroom button) to determine the existence of a triggering event 212.

In some implementations, the triggering event 212 can be associated with a computing device that is remote from the vehicle 102. By way of example, as described herein, a remote computing device(s) 104 can monitor one or more parameter(s) of the vehicle 102 and communicate with the vehicle 102 (e.g., via network(s) 105). In some implementations, the remote computing device(s) 104 (e.g., of a central operations control center) can provide data 216 indicative of a specific vehicle triggering event (e.g., hardware overheating, memory storage low) that may have been remotely identified. In some implementations, the data 216 can indicate that the vehicle 102 is to stop moving (e.g., based on a triggering event, based on a travel condition). In some implementations, the data 216 can indicate that the vehicle 102 is to change operational control (e.g., from autonomous navigation to a manual control mode). The computing device(s) 204 can receive the data 216 provided by the remote computing device 104.

The computing device(s) 204 can be configured to determine one or more action(s) to be performed by one or more system(s) on-board the vehicle 102 in response to the detection of the triggering event 212. The one or more action(s) can be based at least in part on whether the vehicle 102 is in the first operational mode 106A or the second operational mode 106B (e.g., whether the human driver 107 is present in the vehicle 102). The computing device(s) 204 can be configured to provide one or more control signal(s) 218 to one or more system(s) on-board the vehicle 102 (e.g., the vehicle control component(s) 118) to perform the one or more action(s).

For example, the vehicle 102 can be in the first operational mode 106A in which the human driver 107 is present in the vehicle 102. One or more of the action(s) can include allowing the human driver 107 to manually control the vehicle 102. The computing device(s) 204 of the control system 120 can send one or more control signal(s) to cause the vehicle 102 to enter into the manual control mode whereby the vehicle control component(s) 118 operate based at least in part on manual user inputs provided by the human driver 107 (e.g., to the steering wheel, brake, accelerator). In this way, in the event that a triggering event 212 occurs while a human driver 107 is present, the control system 120 can control the failover response of the vehicle 102 to allow the human driver 107 to manually control (e.g., navigate) the vehicle 102.

The failover response of the vehicle 102 can be different in the event that no human driver 107 is present in the vehicle 102. For instance, the vehicle 102 can be in the second operational mode 106B in which the human driver 107 is not present in the vehicle 102. The one or more action(s) determined by the computing device(s) 204 can include stopping a motion of the vehicle 102 (e.g., represented by motion vector 220). For example, the one or more action(s) can include at least one of a deceleration of the vehicle 102 via a braking component 222 and an adjustment of the heading of the vehicle 102 via a steering component 224. To cause the deceleration, the computing device(s) 204 can provide one or more control signal(s) 218 to the braking component 222 to decelerate the vehicle 102 to a stopped position. To cause adjustment of the steering component 224, the computing device(s) 204 can send control signal(s) 218 to maintain the last known good motion command from the autonomy system 116 (and/or the mobility controller 202) and/or to neutral a vehicle throttle. In some implementations (e.g., when the triggering event 212 is not associated with a lack of communicability with the autonomy system 116), the computing device(s) 204 can help steer the vehicle by continuing to provide control signal(s) 218 that are indicative of the control instructions that are received from the autonomy system 116 (and/or the mobility controller 202). Accordingly, the computing device(s) 204 can safely bring the vehicle 102 to a safe position without the presence of a human driver 107.

The computing device(s) 204 can be configured to reset the vehicle 102 such that it can continue to autonomously navigate (e.g., after acting in response to a triggering event). For example, after performance of the one or more action(s) (e.g., to facilitate stopping, to provide manual control), the computing device(s) 204 can receive data 226 indicating that the vehicle 102 is in a ready state, in which the vehicle 102 is ready to return to autonomous navigation (e.g., without interaction from the human driver). In some implementations, the computing device(s) 204 can receive the data 226 indicating that the vehicle 102 is ready to return to an autonomous navigation mode from a computing device located onboard the vehicle 102. For example, such an on-board computing device can be one that identified the occurrence of the triggering event 212 (e.g., critical memory storage error). The on-board computing device can then later identify that the triggering event 212 has been cleared, addressed, etc. (e.g., additional storage available). In some implementations, the data 226 can be provided by a remote computing device 104 (e.g., of an operations computing system monitoring the vehicle 102). In some implementations, the data 226 can be provided via the human machine interface system(s) 112. For example, the human driver 107 can provide user input to an interface (e.g., physical interface, graphical user interface) relinquishing control of the vehicle 102 after the triggering event 212 has been addressed. The computing device(s) 104 can send one or more other control signal(s) 228 to one or more of the system(s) on-board the vehicle 102 (e.g., autonomy system 116, vehicle control component(s) 118) to autonomously navigate the vehicle 102, without interaction from the human driver 107.

Figure 3:
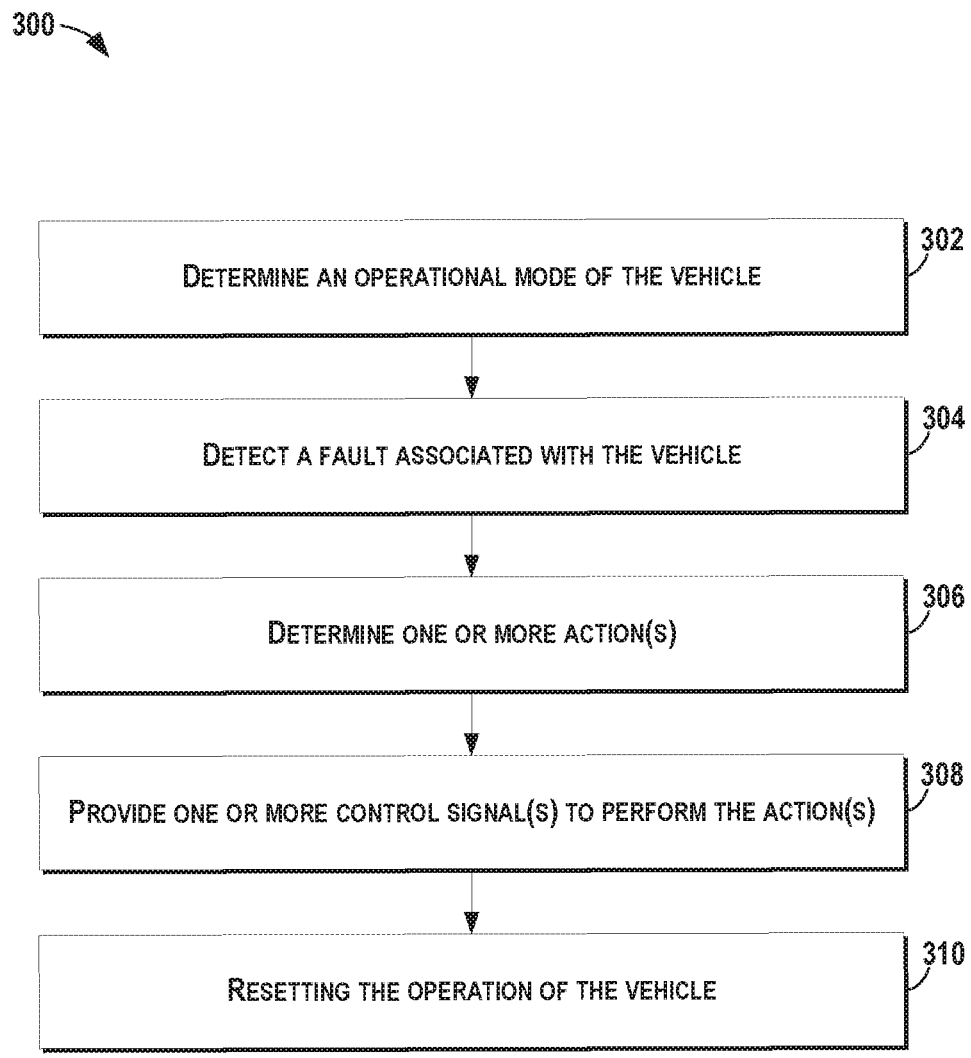
FIG. 3 depicts a flow diagram of an example method of controlling a failover response of a vehicle according to example embodiments of the present disclosure.

FIG. 3 depicts a flow diagram of an example method 300 of controlling a failover response of a vehicle according to example embodiments of the present disclosure. One or more portion(s) of the method 300 can be implemented by one or more computing device(s) such as, for example, the computing device(s) 204 shown in FIGS. 2 and 502 as shown in FIG. 6. Moreover, one or more portion(s) of the method 300 can be implemented as an algorithm on the hardware components of the device(s) described herein (e.g., as in FIGS. 2 and 5) to, for example, control a failover response of the vehicle 102. FIG. 3 depicts elements performed in a particular order for purposes of illustration and discussion. Those of ordinary skill in the art, using the disclosures provided herein, will understand that the elements of any of the methods (e.g., of FIGS. 3-5) discussed herein can be adapted, rearranged, expanded, omitted, combined, and/or modified in various ways without deviating from the scope of the present disclosure.

At (302), the method 300 can include determining an operational mode of a vehicle. For instance, the computing device(s) 204 on-board the vehicle 102 (e.g., autonomous vehicle) can determine an operational mode 106A-B of the vehicle 102. For example, the vehicle 102 can be configured to operate in at least a first operational mode 106A in which a human driver 107 is present in the vehicle 102. The vehicle 102 can be configured to operate in at least a second operational mode 106B in which the human driver 107 is not present in the vehicle 102. In either operational mode, the vehicle 102 can be configured to autonomously navigate without interaction from the human driver 107.

As described herein, the computing device(s) 204 can determine the operational mode 106A-B of the vehicle 102 via communication with another computing device (e.g., on-board, remote from the vehicle). For example, the computing device(s) 204 can receive data 208 indicative of a position associated with an interface 206 on-board the vehicle 102. The vehicle 102 can operate in the first operational mode 106A when the interface 206 is in a first position and/or first state. The vehicle 102 can operate in the second operational mode 106B when the interface 206 is in a second position and/or second state. For example, the interface 206 can be a physical interface (e.g., physical switch interface) that is adjustable between the first position and the second position. Additionally, and/or alternatively, the computing device(s) 204 can determine whether the vehicle 102 is the first operational mode 106A or the second operational mode 106B based at least in part on data 210 indicative of the presence of the human driver 107 in the vehicle 102, as described herein.

Figure 4:
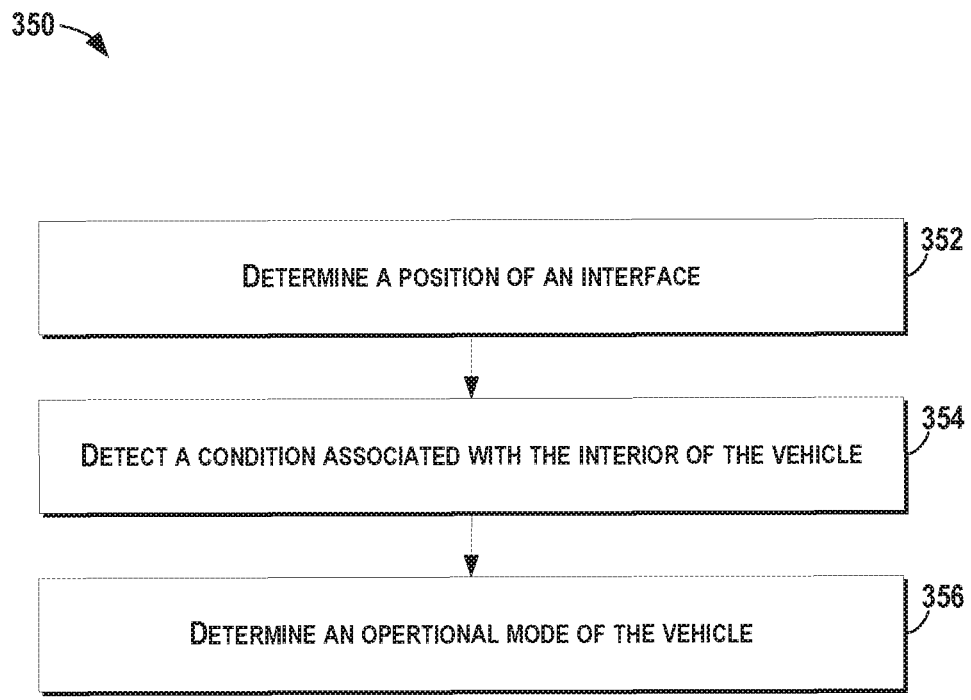
FIG. 4 depicts a flow diagram of an example method of determining an operational mode of a vehicle according to example embodiments of the present disclosure.

FIG. 4 depicts a flow diagram of an example method 350 of determining an operational mode of a vehicle according to example embodiments of the present disclosure. One or more portion(s) of the method 350 can be implemented by one or more computing device(s) such as, for example, the computing device(s) 204 shown in FIG. 2 and 502 as shown in FIG. 6. Moreover, one or more portion(s) of the method 350 can be implemented as an algorithm on the hardware components of the device(s) described herein (e.g., as in FIGS. 2 and 6). FIG. 4 depicts elements performed in a particular order for purposes of illustration and discussion.

At (352), the method 350 can include determining a position of an interface. For instance, the computing device(s) 204 can receive data 208 indicative of a position associated with an interface 206 on-board the vehicle 102. The computing device(s) 204 can determine the position of the interface 206 based at least in part on the data 208. For example, in the event that the interface 206 is in a first position and/or first state, the vehicle 102 can be set to operate in the first operational mode 106A (e.g., with a human driver present). In the event that the interface 206 is in a second position and/or first state, the vehicle 102 can be set to operate in the second operational mode 106B (e.g., without a human driver present).

At (354), the method 350 can include detecting a condition associated with the interior of the vehicle. The computing device(s) 204 can receive data associated with the condition(s) of the interior of the vehicle 102 (e.g., from the sensor(s) 124). For example, the computing device(s) 204 can determine that a weight load is present in the driver's seat of the autonomous vehicle based at least in part on the data from the sensor(s) 124. Additionally, or alternatively, the computing device(s) 204 can determine whether a seat belt associated with the driver seat is in a fastened position based at least in part on the data from the sensor(s) 124. In some implementations, the condition can include a temperature change, a humidity change, a noise level change, etc.

At (356), the method 350 can include determining an operational mode of the vehicle. For instance, the computing device(s) 204 can determine an operational mode 106A-B of the vehicle 102 based at least in part on one or more of the factor(s) associated with the vehicle 102, as determined at (352) and/or (354). By way of example, the computing device(s) 204 can determine whether the vehicle 102 is in a first operational mode 106A (e.g., in which a human driver is present) or a second operational mode (e.g., in which no human driver is present) based at least in part on the interface 206 (e.g., the position/state of the interface) and/or one or more condition(s) associated with the vehicle 102 (e.g., the interior of the vehicle).

Returning to FIG. 3, at (304), the method 300 can include detecting a triggering event associated with the vehicle. For instance, computing device(s) 204 can detect a triggering event 212 associated with the vehicle 102. By way of example, the triggering event 212 can include a defect associated with a communicability between the one or more computing device(s) 204 and another system of the vehicle 102 (e.g., the autonomy system 116, the mobility controller 202). Additionally, or alternatively, the triggering event 212 can be associated with at least one of a user-initiated request and a computing device 104 that is remote from the vehicle 102, as described herein.

At (306), the method can include determining one or more action(s) based at least in part on the triggering event. For instance, the computing device(s) 204 can determine one or more action(s) to be performed by one or more system(s) on-board the vehicle 102 in response to the triggering event 212. The one or more action(s) can be based at least in part on whether the vehicle 102 is in the first operational mode 106A or the second operational mode 106B. For example, in the event that the vehicle 102 is in the first operational mode 106A in which the human driver 107 is present in the vehicle 102, one or more of the action(s) can include allowing the human driver 107 manual control of the vehicle 102. In the event that the vehicle 102 is in the second operational mode 106B in which the human driver 107 is not present in the vehicle 102, one or more of the action(s) can include stopping a motion of the vehicle 102. The computing device(s) 204 can provide one or more control signal(s) to one or more of the system(s) on-board the autonomous vehicle to perform the one or more action(s) in response to the triggering event, at (308).

At (310), the method can include resetting the operation of the vehicle. For instance, the computing device(s) 204 can receive (e.g., after performance of the one or more action(s)), data 226 indicating that the vehicle 102 is in a ready state and is ready to autonomously navigate without interaction from the human driver 107. The data 226 can be provided by a computing device on-board the vehicle 102, a computing device that is remote from the vehicle 102, and/or via user input (e.g., from the human driver 107). The computing device(s) 204 can send one or more other control signal(s) to one or more of the system(s) on-board the vehicle 102 (e.g., the autonomy system 116, the vehicle control component(s) 118) to allow the vehicle 102 to resume motion of the vehicle 102 (e.g., autonomous navigation) without interaction from a human driver 107.

Figure 5:
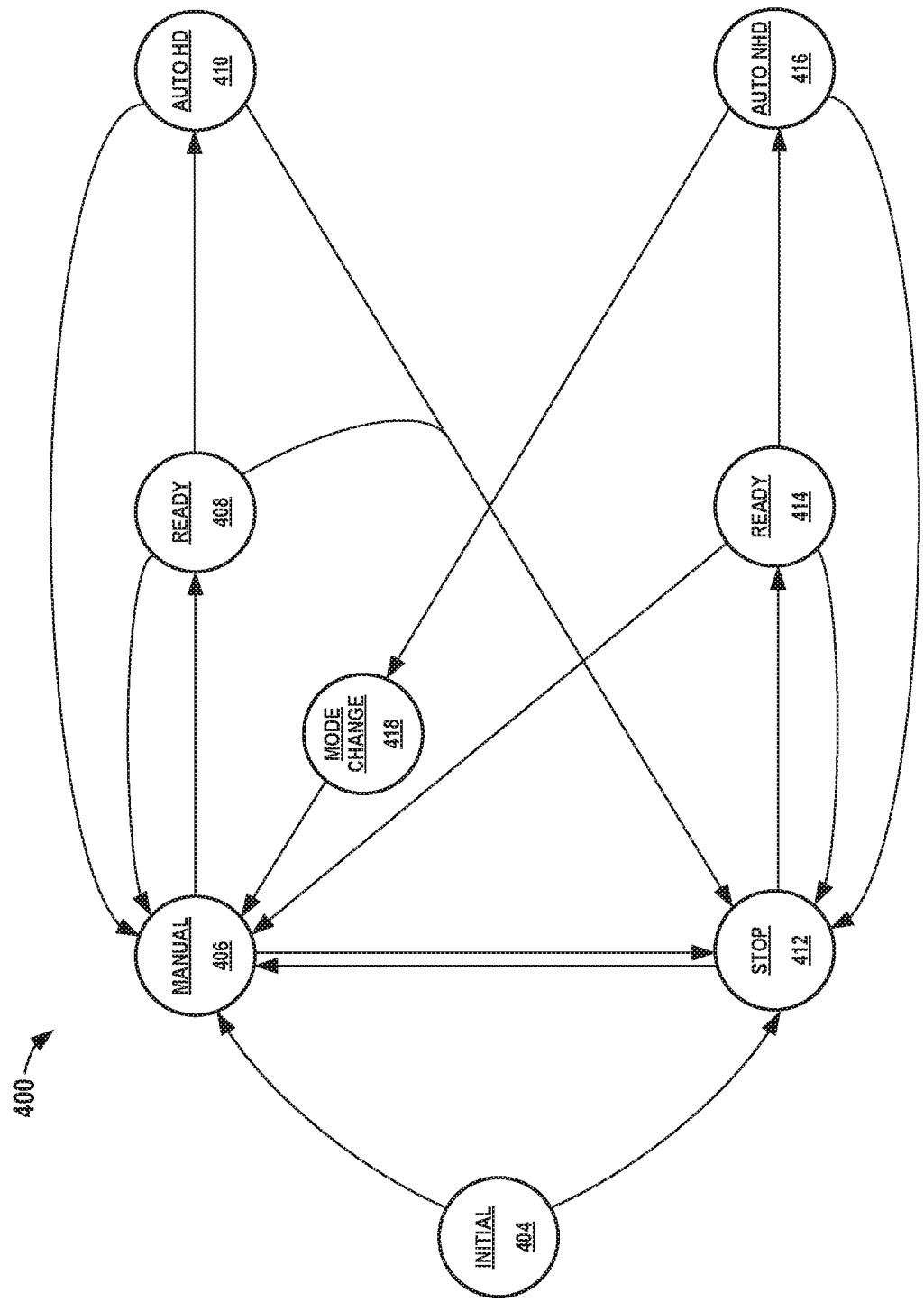
FIG. 5 depicts a diagram of example vehicle states according to example embodiments of the present disclosure.
Figure 6:
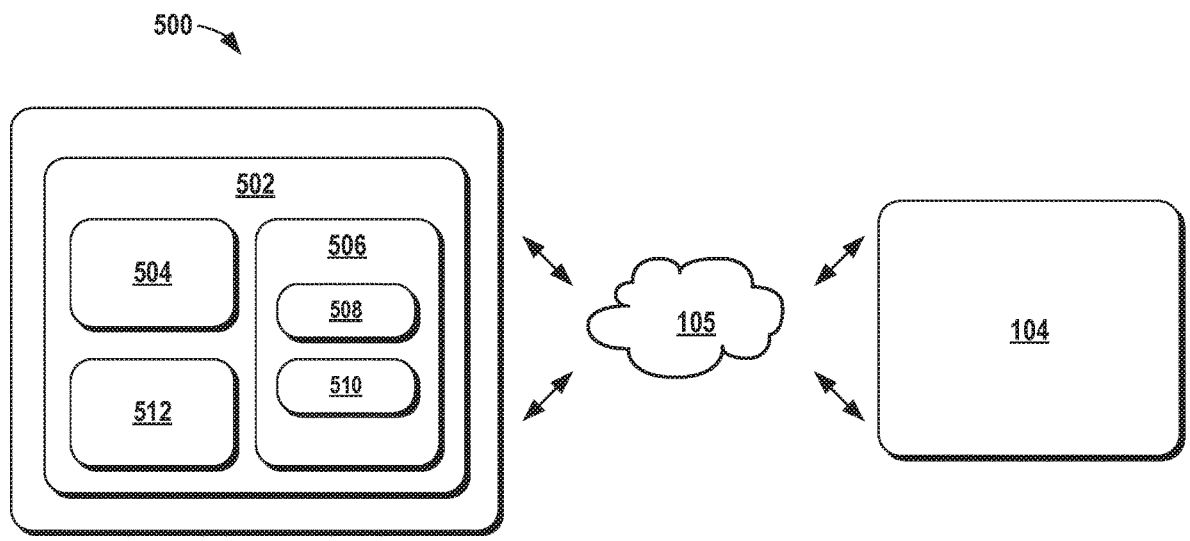
FIG. 6 depicts example system components according to example embodiments of the present disclosure.

FIG. 5 depicts a diagram 400 of example vehicle states according to example embodiments of the present disclosure. One or more portion(s) of the FIG. 5 can be implemented by one or more computing device(s) such as, for example, the computing device(s) 204 and/or control system 120 described herein. Moreover, one or more portion(s) of the FIG. 5 can be implemented as an algorithm on the hardware components of the device(s) described herein (e.g., as in FIGS. 2 and 6). FIG. 5 depicts elements performed in a particular order for purposes of illustration and discussion. Those of ordinary skill in the art, using the disclosures provided herein, will understand that the elements of any of the methods discussed herein can be adapted, rearranged, expanded, omitted, combined, and/or modified in various ways without deviating from the scope of the present disclosure.

At (404), the vehicle 102 can be in an initial state in which the vehicle 102 is operating with or without the presence of a human driver 107. The computing device(s) 204 can determine the failover response of the vehicle 102 based at least in part on a triggering event (e.g., user initiated request via a mushroom button interface) associated with the vehicle 102. The failover response can be based at least in part on whether a human driver 107 is present in the vehicle 102. For example, in the event that a human driver 107 is present in the vehicle 102 (e.g., as indicated by a physical switch interface) when the triggering event is detected, the computing device(s) 204 can cause the vehicle 102 to enter into a manual control mode allowing the human driver 107 manual control of the vehicle 102, at (406).

The computing device(s) 204 can determine and/or receive data 226 indicating that the triggering event has been addressed, cleared, remedied, etc. As such, the vehicle 102 can enter into a ready state at (408), indicating that the vehicle 102 is ready to return to (or to begin) autonomous navigation (e.g., without human intervention). In some implementations, the computing device(s) 204 can perform one or more check procedure(s) before the vehicle 102 enters into the ready state at (408). For example, the computing device(s) 204 can determine whether the human driver's seat belt is fastened, whether all the vehicle doors are closed, whether any interfaces (e.g., physical, soft buttons) requesting manual control are engaged, etc. In the event that another triggering event is detected, and/or any of the check procedure(s) fail, the vehicle 102 can return to the manual control mode, at (406). Otherwise, the vehicle 102 can proceed to an autonomous navigation mode in which the vehicle 102 can navigate without interaction from the human driver 107 (e.g., despite his/her presence in the vehicle), at (410). In some implementations, the human driver 107 can engage with a human machine interface system 112 to cause the vehicle 102 to resume autonomous navigation at (410) from the ready state at (408). In some implementations, a remote computing device 104 can send a signal to the vehicle 102 to cause the vehicle 102 to resume autonomous navigation at (410) from the ready state at (408). If a triggering event is detected while the vehicle 102 is in an autonomous navigation mode, at (410), and a human driver 107 is present in the vehicle 102, the vehicle 102 can return to the manual control mode, at (406).

Additionally, or alternatively, in the event that a human driver 107 is not present in the vehicle 102 (e.g., as indicated by a physical switch interface) when the triggering event is detected, the computing device(s) 204 can stop the vehicle 102 (e.g., provide control signals to cause the vehicle 102 to decelerate to a stopped position), at (412). After the triggering event has been addressed, cleared, remedied, etc., the vehicle 102 can enter into a ready state at (414), indicating that the vehicle 102 is ready to return to (or to begin) autonomous navigation (e.g., without a human driver present). In some implementations, the computing device(s) 204 can perform one or more check procedures before the vehicle 102 enters into the ready state at (414). For example, the computing device(s) 204 can determine whether all the vehicle doors are closed, whether an interface (e.g., physical, soft buttons) requesting manual control are engaged, etc. In the event that another triggering event is detected, and/or any of the check procedures fail, the vehicle 102 can return to a stopped mode, at (412). Otherwise, the vehicle 102 can return to an autonomous navigation mode in which the vehicle 102 can navigate without the human driver 107 present in the vehicle 102, at (416). In some implementations, a computing device on-board the vehicle 102 can determine whether the vehicle 102 is to resume or begin autonomous navigation. In some implementations, a remote computing device 104 can send a signal to the vehicle 102 to cause the vehicle 102 to resume autonomous navigation at (416) from the ready state at (414). If a triggering event is detected while the vehicle 102 is in an autonomous navigation mode, at (416), and no human driver 107 is present in the vehicle 102, the vehicle 102 can stop its motion, at (412).

In some implementations, the vehicle 102 may switch between operational modes 106A-B. For example, if, at any time during states (406), (408), and/or (410), the human driver 107 exits the vehicle 102 (e.g., while parked) and/or a physical interface 206 (e.g., switch interface) is adjusted to indicate that the vehicle 102 is to operate in the second operational mode 106B (e.g., adjusted to the second position), the computing device(s) 204 can cause the vehicle 102 to stop at (412) upon the detection of a triggering event. Additionally, or alternatively, while stopped (e.g., at 412), in autonomous navigation mode (without a human driver), at (416), and/or the ready state at (414), a human driver 107 may enter the vehicle 102 (e.g., while parked) and/or the physical interface 206 may be adjusted to indicate that the vehicle 102 is now in the first operational mode 106A. As such, the computing device(s) 204 can cause the vehicle 102 to enter into the manual control mode (e.g., at (406)) upon the detection of a triggering event. In some implementations, the computing device(s) 204 can perform a check at (418) to confirm that the vehicle 102 is performing an appropriate response. For example, the computing device(s) 204 can perform a check to confirm that a human driver is present in the vehicle 102 in the event that the vehicle 102 is to switch to a manual control mode. In the event that no human driver is present, the computing device(s) 204 can engage another vehicle mechanism that would require human interaction (e.g., parking brake, other mechanism). This type of check can help prevent an erroneous vehicle failover response.

FIG. 6 depicts an example control system 500 according to example embodiments of the present disclosure. The control system 500 can correspond to the control system 120, as described herein. The control system 500 can include the one or more computing device(s) 502, which can correspond to the computing device(s) 204. The computing device(s) 502 can include one or more processor(s) 504 on-board the vehicle 102 and one or more memory device(s) 506 on-board the vehicle 102. The one or more processor(s) 504 can be any suitable processing device such as a microprocessor, microcontroller, integrated circuit, an application specific integrated circuit (ASIC), a digital signal processor (DSP), a field-programmable gate array (FPGA), logic device, one or more central processing units (CPUs), processing units performing other specialized calculations, etc. The processor(s) 504 can be a single processor or a plurality of processors that are operatively and/or selectively connected. The memory device(s) 506 can include one or more non-transitory computer-readable storage media, such as RAM, ROM, EEPROM, EPROM, flash memory devices, magnetic disks, etc., and/or combinations thereof.

The memory device(s) 506 can store information that can be accessed by the one or more processor(s) 504. For instance, the memory device(s) 506 on-board the vehicle 102 can include computer-readable instructions 508 that can be executed by the one or more processor(s) 504. The instructions 508 can be software written in any suitable programming language or can be implemented in hardware. Additionally, or alternatively, the instructions 508 can be executed in logically and/or virtually separate threads on processor(s) 504. The instructions 508 can be any set of instructions that when executed by the one or more processor(s) 504 cause the one or more processor(s) 504 to perform operations.

For example, the memory device(s) 506 on-board the vehicle 102 can store instructions 508 that when executed by the one or more processor(s) 504 on-board the vehicle cause the one or more processor(s) 504 (and/or the control system 500) to perform operations such as any of the operations and functions of the computing device(s) 204 or for which the computing device(s) 204 are configured, as described herein, the operations for controlling the failover response of a vehicle (e.g., one or more portion(s) of methods 300, 400), and/or any other operations or functions for controlling a failover response of an autonomous vehicle, as described herein.

The one or more memory device(s) 506 can store data 510 that can be retrieved, manipulated, created, and/or stored by the one or more processor(s) 504. The data 510 can include, for instance, data associated with the vehicle 102, data acquired by the data acquisition system(s), map data, data associated with the vehicle operational mode, data associated with a vehicle ready state, data associated with a triggering event, data associated with user input, data associated with one or more action(s) and/or control signals, data associated with users, and/or other data or information. The data 510 can be stored in one or more database(s). The one or more database(s) can be split up so that they are located in multiple locales on-board the vehicle 102. In some implementations, the computing device(s) 502 can obtain data from one or more memory device(s) that are remote from the vehicle 102.

The computing device(s) 502 can also include communication interface 512 used to communicate with one or more other system(s) on-board the vehicle 102 and/or computing device(s) that are remote from the vehicle (e.g., 104). The communication interface 512 can include any suitable components for interfacing with one or more network(s) (e.g., 105), including for example, transmitters, receivers, ports, controllers, antennas, or other suitable hardware and/or software.

The technology discussed herein makes reference to computing devices, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, computer-implemented processes discussed herein can be implemented using a single computing device or multiple computing devices working in combination. Databases and applications can be implemented on a single system or distributed across multiple systems. Distributed components can operate sequentially or in parallel.

Furthermore, computing tasks discussed herein as being performed at computing device(s) remote from the vehicle (e.g., the operations computing system and its associated computing device(s)) can instead be performed at the vehicle (e.g., via the vehicle computing system). Such configurations can be implemented without deviating from the scope of the present disclosure.

While the present subject matter has been described in detail with respect to specific example embodiments and methods thereof, it will be appreciated that those skilled in the art, upon attaining an understanding of the foregoing can readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A computer-implemented method of controlling autonomous vehicle failover response, comprising:
    determining, by a computing system comprising one or more computing devices, that a human operator is operating an autonomous vehicle or that the human operator is not operating the autonomous vehicle;
    detecting, by the computing system, a triggering event associated with the autonomous vehicle;

determining, by the computing system, one or more actions to be performed by the autonomous vehicle in response to the triggering event, wherein the one or more actions are based at least in part on whether the human operator is operating the autonomous vehicle; and causing, by the computing system, the autonomous vehicle to perform the one or more actions in response to the triggering event.

2. The computer-implemented method of claim 1, wherein the autonomous vehicle is configured to autonomously navigate without interaction from the human driver.

3. The computer-implemented method of claim 2, wherein the human driver is not operating the autonomous vehicle, and wherein the one or more actions comprise autonomously reducing the speed of the autonomous vehicle and stopping a motion of the autonomous vehicle.

4. The computer-implemented method of claim 3, wherein the one or more actions comprise autonomously adjusting the heading of the autonomous vehicle.

5. The computer-implemented method of claim 3, further comprising:

causing, by the computing system, the autonomous vehicle to resume motion of the autonomous vehicle without the presence of the human driver.

6. The computer-implemented method of claim 1, wherein the triggering event comprises a defect associated with an onboard system of the autonomous vehicle.

7. The computer-implemented method of claim 1, wherein the triggering event is associated with a request initiated by a passenger of the autonomous vehicle.

8. The computer-implemented method of claim 1, wherein the human driver is operating the autonomous vehicle, and wherein one or more of the actions comprise allowing the human driver manual control of the autonomous vehicle.

9. The computer-implemented method of claim 1, wherein determining that the human driver is operating the autonomous vehicle or that the human driver is not operating the autonomous vehicle comprises:

receiving, by the computing system, data indicative of a position associated with a physical interface on-board the autonomous vehicle, wherein the autonomous vehicle is to operate in a first operational mode when the physical interface is in a first position, and wherein the autonomous vehicle is to operate in a second operational mode when the physical interface is in a second position.

10. The computer-implemented method of claim 9, wherein determining that the human operator is not operating the autonomous vehicle comprises determining that the human operator is not present in the autonomous vehicle.

11. A computing system for controlling autonomous vehicle failover response, comprising:

one or more processors; and one or more memory devices on-board the autonomous vehicle, the one or more memory devices storing instructions that when executed by the one or more processors cause the computing system to perform operations, the operations comprising:

detecting a triggering event associated with an autonomous vehicle;

determining one or more actions to be performed by the autonomous vehicle in response to the detection of the triggering event, wherein the one or more actions are based on whether or not a human operator is operating the autonomous vehicle; and providing one or more control signals to one or more systems on-board the autonomous vehicle to initiate the one or more actions.

12. The computing system of claim 11, wherein the one or more systems on-board the autonomous vehicle comprise one or more vehicle control components, and wherein the one or more vehicle control components comprise a brake component and a steering component.

13. The computing system of claim 11, wherein the human driver is not operating the autonomous vehicle, and wherein one or more of the actions comprise at least one of a deceleration of the autonomous vehicle via the braking component and an adjustment of the heading of the autonomous vehicle via the steering component.

14. The computing system of claim 11, wherein the human driver is not operating the autonomous vehicle, and wherein one or more of the actions comprise allowing the human driver to manually control the autonomous vehicle.

15. The computing system of claim 11, wherein the human driver is not present in the autonomous vehicle, and wherein the autonomous vehicle is configured to autonomously navigate without interaction from the human operator, and wherein the operations comprise:

receiving, after performance of the one or more actions, data indicating that the autonomous vehicle is ready to autonomously navigate without interaction from the human operator; and communicating one or more other control signals to cause the autonomous vehicle to autonomously navigate without interaction from the human operator.

16. The computing system of claim 11, wherein the triggering event is associated with a lack of communicability with an autonomy system of the autonomous vehicle.

17. An autonomous vehicle comprising:

one or more processors; and one or more memory devices, the one or more memory devices storing instructions that when executed by the one or more processors cause the one or more processors to perform operations, the operations comprising:

determining that a human operator is operating the autonomous vehicle or that the human operator is not operating the autonomous vehicle;

detecting a triggering event associated with the autonomous vehicle;

determining one or more actions to be performed by the autonomous vehicle in response to the triggering event, wherein the one or more actions are based at least in part on whether or not the human driver is operating the autonomous vehicle; and providing one or more control signals to initiate the one or more actions.

18. The autonomous vehicle of claim 17, wherein determining that the human operator is operating the autonomous vehicle or that the human operator is not operating the autonomous vehicle comprises:

obtaining data indicative of a presence of the human operator in the autonomous vehicle, wherein the presence of the human operator is detectable based at least in part on a change in a condition associated with the interior of the autonomous vehicle.

19. The autonomous vehicle of claim 18, wherein the condition associated with the autonomous vehicle comprises at least one of a weight load in a seat of the autonomous vehicle, a position of a seat belt of the autonomous vehicle, or an adjustment of a physical interface of the autonomous vehicle.

20. The autonomous vehicle of claim 17, wherein determining that the human operator is operating the autonomous vehicle comprises determining that the autonomous vehicle is in a semi-autonomous operational mode that permits operation of the autonomous vehicle by the human operator.

* * * * *